US00PP19071P2

(12) United States Plant Patent

Bak et al.

(10) Patent No.: US PP19,071 P2

(45) Date of Patent: Aug. 5, 2008

(54) *VRIESEA* PART NAMED 'MAGIC'

(50) Latin Name: ***Vriesea* sp.**
Varietal Denomination: Magic

(75) Inventors: Elly Bak, Rijsenhout (NL); Nico D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 0 days.

(21) Appl. No.: 11/812,120

(22) Filed: Jun. 15, 2007

(51) Int. Cl.
*A01H 5/00* (2006.01)

(52) U.S. Cl. ..... Plt./370

(58) Field of Classification Search ..... Plt./370
See application file for complete search history.

*Primary Examiner*—Kent L Bell
(74) *Attorney, Agent, or Firm*—Foley & Lardner LLP

(57) ABSTRACT

A new and distinct *Vriesea* plant named 'Magic' characterized as a funnel-form rosette plant, measuring about 45 cm to 55 cm in height (when flowering) and 35 cm to 45 cm in diameter; producing compound, red-purple in color (RHS 59C), bipinate spike inflorescence, measuring about 35 cm in height and about 18 cm in diameter; about 6 to 9 branches; and yellow-green foliage, measuring about 30 cm in length and about 5.0 cm to 5.5 cm in width.

2 Drawing Sheets

Latin name of the genus and species of the plant claimed: *Vriesea* sp.
Variety denomination: 'Magic'.

BACKGROUND OF THE INVENTION

The present invention relates to a new and distinct cultivar of *Vriesea* plant, botanically known as *Vriesea* sp., hereinafter referred to by the cultivar name 'Magic'. The genus of *Vriesea* belongs to the Bromeliaceae family.

The new *Vriesea* cultivar is a product of a planned breeding program conducted by the inventors, Elly Bak and Nico D. M. Steur, in Assendelft, The Netherlands. The objective of the breeding program is to develop a new *Vriesea* variety good growing habit and attractive inflorescence.

The new *Vriesea* cultivar 'Magic' originated from a cross-made in a controlled breeding program by the Inventors in 1989 in Assendelft, The Netherlands. The female or seed parent is the *Vriesea* sp cultivar designated '8945216' (unpatented). The male or pollen parent is the *Vriesea* sp. cultivar designated '84100' (unpatented). 'Magic' was discovered and selected by the inventors in May of 1993, as a single flowering plant within the progeny of the stated cross in a controlled environment in Assendelft, The Netherlands.

Asexual reproduction of the new cultivar 'Magic' performed by vegetative means by tissue culture was first performed in 1997, in Assendelft, The Netherlands. The first 'Magic' plants propagated through the use of tissue culture flowered in 2002, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'Magic' which in combination distinguish this *Vriesea* as a new and distinct cultivar:

1. Funnel-form rosette plant, measuring about 45 cm to 55 cm in total height (when flowering) and about 35 cm to 40 cm in diameter;
2. Compound, red-purple in color (RHS 59C), bipinate spike inflorescence, measuring about 35 cm in height and about 18 cm in diameter;
3. About 6 to 9 branches; and
4. Yellow-green foliage, measuring about 30 cm in length and about 5.0 cm to 5.5 cm in width.

Plants of the parents, '8945216' (unpatented) and '84100' (unpatented) are no longer available to provide a detailed botanical comparison with the new *Vriesea* cultivar 'Magic'. The new cultivar 'Magic' differs primarily from plants of the parental cultivars by exhibiting a more branched inflorescence, lilac in color.

Of the many commercial cultivars known to the present inventors, the most similar in comparison to the new *Vriesea* cultivar 'Magic' is the *Vriesea* cultivar designated 'Style' (as described in U.S. Pat. No. 18,176). Plants of the new cultivar 'Magic' differ from plants of 'Style' primarily in inflorescence color.

BRIEF DESCRIPTION OF THE PHOTOGRAPH

The accompanying photograph illustrates the overall appearance of the new *Vriesea* cultivar 'Magic' showing the colors as true as is reasonably possible with colored reproductions of this type. Colors in the photograph may differ slightly from the color values cited in the detailed botanical description which accurately describes the color of 'Magic'.

DETAILED BOTANICAL DESCRIPTION

Figure 1:
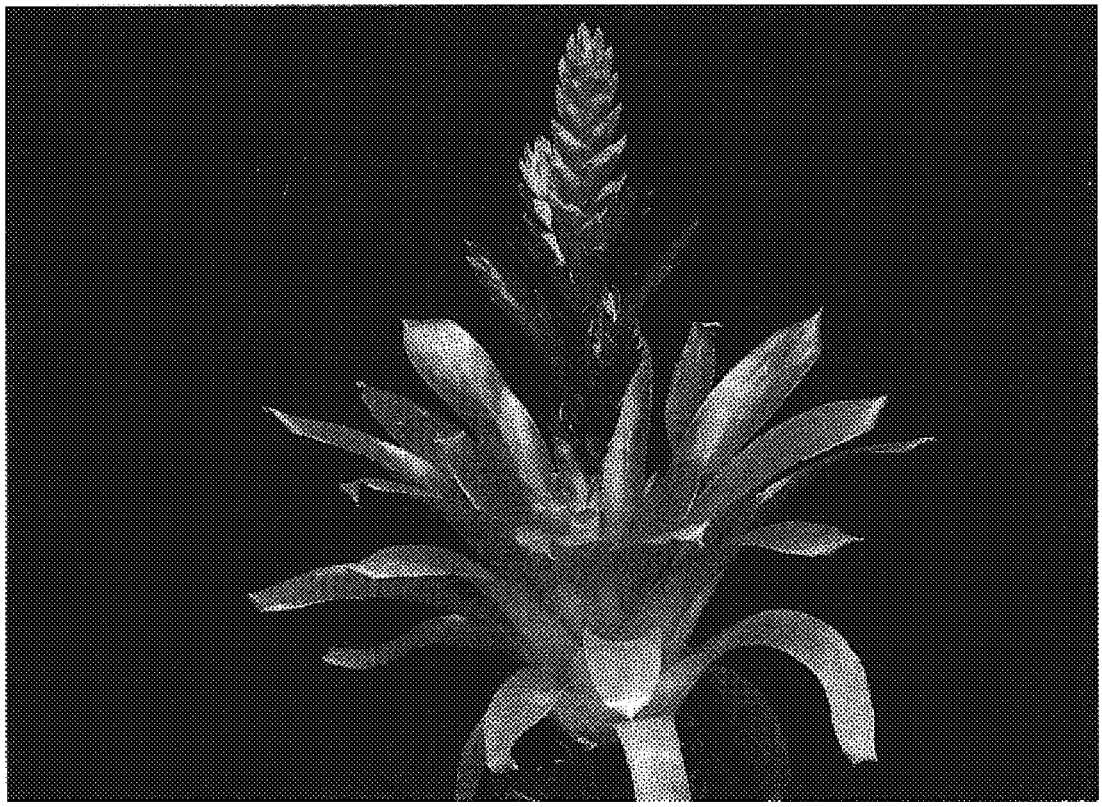
FIG. 1 shows a side view perspective of a typical potted flowering plant of 'Magic' at about 17 months of age.
Figure 2:
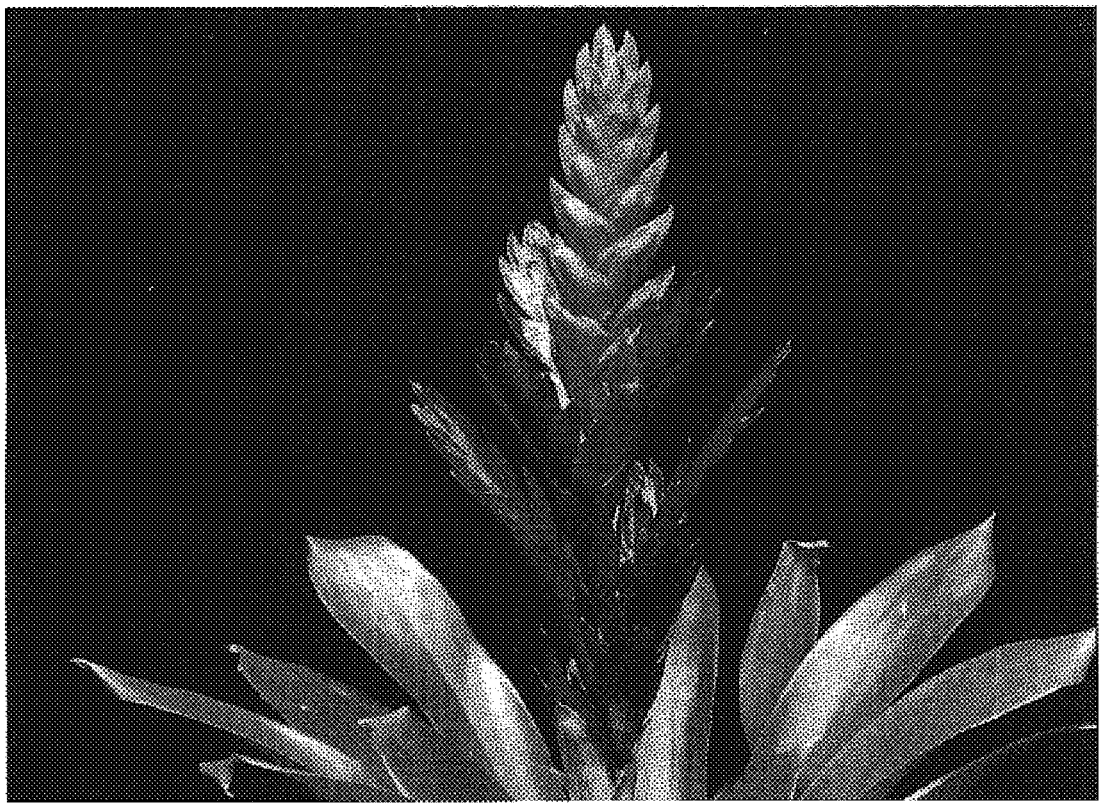
FIG. 2 shows a close-up side view perspective of a typical potted flowering plant of 'Magic' at about 17 months of age.

'Magic' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Vriesea* cultivar as grown in a greenhouse in Assendelft, The Netherlands, under conditions which closely approximate those generally used in commercial practice. Plants of 'Magic' were grown in a greenhouse with day temperatures ranging from 20° C. to 28° C. and night temperatures ranging from 18° C. to 23° C. No artificial lighting or photoperiodic treatments were conducted, but plants of 'Magic' are forced into flowering by adding acetylene. The following fertilizer is added when growing plants of 'Magic': 1 part nitrogen, 0.6 parts phosphor, 2 parts Kalium and 0.1 parts magnesium.

Color references are made to The Royal Horticultural Society Colour Chart (R.H.S.), except where general colors of ordinary significance are used. Color values were taken under daylight conditions in a greenhouse in Assendelft, The Netherlands. The age of the plants of 'Magic' described is about 17 months.

Classification:

*Botanical.*—*Vriesea* sp.

Parentage:

*Female parent.*—*Vriesea* sp. cultivar designated '8945216' (unpatented).

*Male parent.*—*Vriesea* sp. cultivar designated '84100' (unpatented).

Propagation: Tissue culture.

Plant:

*General appearance and form.*—Height: About 45 cm to 55 cm (when flowering). Width: About 35 to 45 cm. Shape: Funnel form rosette.

*Growth habit.*—Stemless.

*Plant vigor.*—Good.

*Flowering season.*—A fully grown plant can flower year round, starting 15-17 weeks after induction of natural light or trough treatment with acetylene.

*Cold tolerance.*—Frost tender. Temperatures below 5° C. may damage plants.

*Fragrance.*—None.

Foliage:

*Quantity.*—About 25 to 35.

*Size of mature leaf.*—Length: About 30 cm. Width: About 5.0 cm to 5.5 cm.

*Overall shape.*—Broad and linear.

*Apex shape.*—Abruptly acuminate.

*Base shape.*—Strap-like around central axis.

*Margin.*—Entire.

*Texture.*—Smooth and glabrous.

*Color.*—Leaf color can vary somewhat depending on growing conditions. Upper Surface: Mature leaf: Yellow-green, RHS 147 A. Immature leaf: Yellow-green, RHS 146A. Lower Surface: Mature leaf: Yellow-green, RHS 147 B. Immature leaf: Yellow-green, RHS 146A.

*Venation.*—Pattern: Irregular, traverse lines.

Inflorescence:

*Quantity and form.*—1 flower per floral bract, typical for the genus *Vriesea;* flowering is normally in progression from base to tip of scape.

*Shape.*—Bipinate spike (main spike about 19 cm in length and about 5.5 cm in width; side spike about 14 cm in length and about 4.5 cm in width).

*Size.*—Height: About 35 cm. Diameter: About 18 cm.

*Color.*—Red-purple, RHS 59C.

*Corolla.*—Form: Long and narrow, petals and sepals fused at the base around the ovary. Number: About 80 to 100 depending on the size of plant.

*Petals.*—Number: 3 per flower. Length: About 4.5 cm. Width: About 0.8 cm. Overall Shape: Ligulate. Apex Shape: Cuspidate. Base Shape: Fused. Color: Upper surface: Yellow, RHS 3A. Lower surface: Yellow, RHS 3A. Sepals: Number: 3 per flower. Length: About 3 cm. Width: About 0.9 cm. Overall Shape: Ligulate. Apex Shape: Acute. Base Shape: Fused. Color: Translucent, closest to RHS 5A. Branches: Quantity: About 6 to 9. Length: About 10 cm to 18 cm. Width: About 5.5 cm. Color: Red-purple, RHS 59C. Bracts: Quantity of bracts on main spike: About 12 to 26. Arrangement: Alternate. Size: Length: About 3.5 cm to 4.5 cm. Width: About 2.5 cm to 3.5 cm. Overall shape: Ovate. Color: Red-purple, RHS 59C.

Reproductive organs:

*Androecium.*—Stamen: Number: 6 per flower. Length: About 3.5 cm. Diameter: About 0.1 cm. Color: Yellow, RHS 11C. Anther: Length: About 0.8 cm. Color: Yellow, RHS 11C. Pollen: Amount: Scarce. Color: Yellow, RHS 5A.

*Gynoecium.*—Pistil: Number: 1 per flower. Length: About 4.5 cm. Stigma: Shape: 3-parted. Width: About 0.4 cm. Color: Yellow-green, RHS 144B. Style: Length: About 4.5 cm. Color: Yellow, RHS 11C. Ovary: Shape: Conical. Length: About 0.8 cm. Diameter: About 0.3 cm. Color: Yellow, RHS 11C.

Seeds: None produced.

Fruit: None produced.

Disease/pest resistance: No information is currently available.

Disease/pest susceptibility: No information is currently available.

We claim:

1. A new and distinct *Vriesea* plant named 'Magic', as illustrated and described herein.

* * * * *